United States Patent [19]

Skalabrin

[11] 4,389,370
[45] Jun. 21, 1983

[54] LOW GOLD CONTENT DENTAL ALLOY

[76] Inventor: Nicholas J. Skalabrin, 1004 Puget Dr., SE., Port Orchard, Wash. 98366

[21] Appl. No.: 261,000

[22] Filed: May 6, 1981

[51] Int. Cl.³ .............................................. C22C 5/06
[52] U.S. Cl. ................................................. 420/505
[58] Field of Search .......................... 75/173 R, 172 G; 433/207, 222; 420/505

[56] References Cited

U.S. PATENT DOCUMENTS

| 1,296,938 | 3/1919 | Fahrenwald | 75/173 R |
|---|---|---|---|
| 2,198,400 | 4/1940 | Williams | 75/173 C |
| 2,716,605 | 8/1955 | Schatz | 75/172 G |
| 3,667,936 | 6/1972 | Katz | 75/134 N |
| 3,767,391 | 10/1973 | Tuccillo et al. | 75/134 C |
| 3,819,366 | 6/1974 | Katz | 75/172 R |
| 3,929,475 | 12/1975 | Ingersoll | 75/173 R |
| 4,007,040 | 2/1977 | Kropp | 75/165 |
| 4,012,228 | 3/1977 | Dudek et al. | 75/134 C |
| 4,179,288 | 12/1979 | Prosen | 75/172 G |
| 4,194,907 | 3/1980 | Tsai | 75/134 N |

Primary Examiner—L. Dewayne Rutledge
Assistant Examiner—David A. Hey

[57] ABSTRACT

The present invention provides substantially lower cost dental alloys which may be used in producing full crowns, inlays, onlays, ¾ crowns, and fixed bridges. The alloys can be closely adapted to tooth structure by the use of normal intra-oral dental finishing techniques. The alloys of the present invention have melting points around 1900° F. The alloy consists of Gold 10%, Palladium 22%, Tin 8%, Silver 59%, Zinc 1%.

1 Claim, No Drawings

LOW GOLD CONTENT DENTAL ALLOY

BACKGROUND OF THE INVENTION

Due to the rapid escalating changes in the price of gold and the consequent cost to dental patients, a great need exists for a low gold content dental alloy which, however, still exhibits the properties needed for excellent clinical results. Many of the present low gold or no gold content dental alloys on the market do not exhibit properties which allow them to be closely adapted to tooth structure and therefore cannot be used for inlays, onlays, and ¾ crowns. Furthermore, in the case of nickel-chromium base alloys, some have been implicated in allergic response reactions in patients. It was important to design an alloy utilizing metals which have been used in dentistry for a great period of time insuring a record of low incidence of toxicity and allergic responses.

It was also important to design an alloy which could be utilized with present equipment and the normal standard techniques so as to prevent added costs of new equipment and training.

To my knowledge, the following are the most pertinent U.S. Patents relating to the subject matter of this application:
U.S. Pat. No. 1,296,938
U.S. Pat. No. 2,198,400
U.S. Pat. No. 2,716,605
U.S. Pat. No. 3,929,475
U.S. Pat. No. 3,667,936
U.S. Pat. No. 3,767,391
U.S. Pat. No. 3,819,366
U.S. Pat. No. 4,007,040
U.S. Pat. No. 4,012,228
U.S. Pat. No. 4,179,288
U.S. Pat. No. 4,194,907

Together with the references made of record during the prosecution of such patents.

In my opinion, none of the foregoing U.S. Patents anticipate the invention herein disclosed and claimed, nor would it have been obvious to a man skilled in the art to evolve this invention from such prior art patents.

SUMMARY OF THE INVENTION

This invention deals with the discovery of a low gold content dental alloy which possesses mechanical and clinical properties similar to high gold content dental alloys. It incorporates the following constituents in percentage by weight:

| CONSTITUENTS | PROPORTIONS |
|---|---|
| Gold | 10% |
| Palladium | 22% |
| Silver | 59% |
| Tin | 8% |
| Zinc | 1% |

DETAILED DESCRIPTION OF THE INVENTION

In the extensive investigation and experimentation used to derive the composition of this alloy, the goal of excellent clinical handling properties was primary. In particular, the ability to be closely adapted to tooth structure by the use of normal intra-oral dental finishing techniques, making it especially suitable for inlays, onlays, ¾ crowns, full crowns and fixed bridges. Early on it was discovered that in the case of low gold content dental alloys, the standard laboratory tests now used to test dental alloys do not directly relate to their clinical handling properties. The Brinell Hardness tests and the Elongation tests which were used to indicate the ability of an alloy to be closely adapted to tooth structure no longer apply. A test standard which more closely relates to the clinical handling characteristics of the alloy needed to be devised. To closely adapt dental alloy to tooth structure, the standard intra-oral technique is to use abrasive stones and disks rotating from the alloy to the tooth structures beginning with the coarser grits and proceeding to finer grits as the alloy is drawn onto the tooth structure. The finished alloy-tooth structure margin should be so finely finished that a fine dental explorer instrument drawn from the tooth structure to the alloy cannot detect the margin. As a comparison dental alloy, Type III dental gold was selected as an alloy possessing the minimum requirements for adaptability to tooth structure. In experimenting with abrasive stones drawn across the cross section of cast 14ga test rods, it was found that there was a characteristic that could consistently be used as a comparison test between alloys which directly related to the method of clinical application of the alloys. This characteristic was the formation of a grinding fin. With the use of a standard grinding stone in a rotating instrument, at identical pressure and RPM, a comparison can be made of the measurable length of grinding fins produced. At the preferred alloy composition by weight of Gold 10%, Palladium 22%, Silver 59%, Tin 8%, and Zinc 1%, grinding fins were closely comparable to Type III Dental Gold.

The various elements of this alloy and their contribution and range of percentage by weight are as follows:
- 10% Gold—Gold at this percentage results in a great savings in cost of materials yet allows for a light gold color, adds to tarnish resistance, ductility and maleability.
- 22% Palladium—Extensive clinical tests were made to determine that this was the minimum amount needed of this element in order to insure tarnish resistance. It also adds to hardness.
- 8% Tin—Extensive laboratory tests were made to determine that this was the maximum amount of this element which could be used before adverse eutectic layering occured resulting in fracturing of the alloy under light forces. It also adds to maleability and lowers melting temperatures.
- 59% Silver—Adds to ductility and maleability.
- 1% Zinc—Aids in alloying by action as a deoxidizer.

The alloys have a Brinell Hardened number in the range of 169S-190H, a melting range of 1850°-1925° F.

In the manufacturing process, the elements are melted together in an electric induction furnace under a curtain of burning hydrogen gas. A lid is placed on the furnace and through a fine opening a thin stream of alloy is poured from the tipped furnace into a vat of running tap water against a submerged, inclined graphite plate. As the stream of molten alloy strikes the inclined graphite plate, it disperses and solidifies into small spheres. This is the final form of the manufactured alloy. The small spheres are convenient for weighing and melting in normal dental laboratory procedures.

An alternate method of manufacture is by making the melt in a hinged casting crucible using an oxy-acetylene torch. After all elements have fused, the alloy is fluid and while maintaining contact with the oxy-acetylene flame, the crucible is hinged up and a fine stream of molten alloy is dropped through the water bath against the inclined graphite plate. The same spherical shapes will result as in the previous method.

As earlier set forth, one of the goals of the invention is its ability to be utilized with present equipment and normal standard techniques. Through extensive test formulation, the invention will accept all dental gold solders, can be used with hydroscopic or thermal expansion investments, and melts and casts with the use of a standard compressed air-natural gas or compressed air-propane torch.

What is claimed is:

1. An alloy especially designed to be used for inlays, onlays, ¾ crowns and bridges, wherein by weight the Gold content is 10%, the Palladium 22%, the Silver 59%, the Tin 8%, and the Zinc 1%.

* * * * *